US012566181B2

(12) United States Patent
Ildstad et al.

(10) Patent No.: US 12,566,181 B2
(45) Date of Patent: Mar. 3, 2026

(54) METHODS AND COMPOSITIONS FOR DETERMINING THE POTENCY OF A THERAPEUTIC CELLULAR COMPOSITION

(71) Applicants:University of Louisville Research Foundation, Louisville, KY (US); ImmunoFree, Inc., Greenwich, CT (US)

(72) Inventors: Suzanne T. Ildstad, Prospect, KY (US); Andreas Katopodis, Basel (CH); Vladimir Senyukov, Basel (CH); Margit Jeschke, Basel (CH)

(73) Assignees: ImmunoFree, Inc., Greenwich, CT (US); University of Louisville Research Foundation, Louisville, KY (US)

( * ) Notice: Subject to any disclaimer, the term of this patent is extended or adjusted under 35 U.S.C. 154(b) by 0 days.

(21) Appl. No.: 15/913,520

(22) Filed: Mar. 6, 2018

(65) Prior Publication Data

US 2018/0252729 A1     Sep. 6, 2018

Related U.S. Application Data

(60) Provisional application No. 62/467,420, filed on Mar. 6, 2017.

(51) Int. Cl.
| | |
|---|---|
| *G01N 33/68* | (2006.01) |
| *C07K 16/18* | (2006.01) |
| *C07K 16/28* | (2006.01) |
| *G01N 33/50* | (2006.01) |

(52) U.S. Cl.
CPC ......... *G01N 33/6872* (2013.01); *C07K 16/18* (2013.01); *C07K 16/2809* (2013.01); *C07K 16/2815* (2013.01); *G01N 33/5005* (2013.01); *G01N 2333/4703* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 5,772,994 | A | 6/1998 | Ildstad et al. |
| 8,242,248 | B2 | 8/2012 | Soper et al. |
| 8,632,768 | B2 | 1/2014 | Ildstad et al. |
| 9,452,184 | B2 | 9/2016 | Ildstad et al. |
| 2010/0086951 | A1 | 4/2010 | Hedley et al. |
| 2010/0297123 | A1 | 11/2010 | Garrison et al. |
| 2013/0122015 | A1 | 5/2013 | Getts et al. |
| 2014/0199273 | A1 | 7/2014 | Cesano et al. |
| 2015/0147304 | A1 | 5/2015 | Merkenschlager |
| 2016/0235793 | A1 | 8/2016 | Thorne |
| 2021/0140975 | A1 | 5/2021 | Ildstad et al. |

FOREIGN PATENT DOCUMENTS

| | | |
|---|---|---|
| CN | 1871519 | 11/2006 |
| CN | 101027557 | 8/2007 |
| CN | 101421625 | 4/2009 |
| CN | 102792160 | 11/2012 |
| JP | 2012-504970 | 3/2012 |
| JP | 2016-527920 | 9/2016 |
| WO | WO 2003/012060 | 2/2003 |
| WO | WO 2007/090032 | 8/2007 |
| WO | WO 2012/024546 | 2/2012 |

OTHER PUBLICATIONS

PCT International Preliminary Report on Patentability in International Appln. No. PCT/US2018/021149, dated Sep. 10, 2019.

International Search Report and Written Opinion in International Application No. PCT/US2018/021149, date of mailing May 18, 2018, 15 pages.

Porat et al., "Critical elements in the development of cell therapy potency assays for ischemic conditions", Cytotherapy, 17: 817-831, 2015.

Salmond et al., "MAPK, Phosphatidylinositol 3-Kinase, and Mammalian Target of Rapamycin Pathways Converge at the Level of Ribosomal Protein S6 Phosphorylation to Control Metabolic Signaling in CDS T Cells", The Journal of Immunology, 183(11):7388-7397, 2009.

Theilgaard-Monch et al., "Flow cytometric assessment of lymphocyte subsets, lymphoid progenitors, and hematopoietic stem cells in allogeneic stem cell grafts," Bone Marrow Transplantation, 2001, 28: 1073-1082.

Yu et al., "Regulation of T-cell activation and migration by the kinase TBK1 during neuroinflammation," Nature Communications, 2015, 6: 1-13.

Cornish et al., "Differential regulation of T-cell growth by IL-2 and IL-15," Blood, Jul. 15, 2006, 108(2): 600-608.

Jeurink et al., "T cell responses in fresh and cryopreserved peripheral blood mononuclear cells: kinetics of cell viability, cellular subsets, proliferation, and cytokine production," Cryobiology, 2008, 57(2):91-103.

Basu et al., "Cell-based therapeutic productions: potency assay development and application," Regen. Med., 2014, 9(4): 497-512.

Bravery et al., "Potency assay development for cellular therapy products: an ISCT* review of the requirements and experiences in the industry," Cytotherapy, 2013, 15: 9-19, 20 pages.

Setoguchi et al., "mTOR signaling promotes a robust and continuous production of IFN-γ by human memory CD8⁺ T cells and their proliferation," European Journal of Immunology, Jan. 2, 2015, 45(3):893-902.

Barten et al., "145 Novel Immunoassay for Therapeutic Drug Monitoring of mTOR-Inhibitors after Heart and Lung Transplantation," J. of Heart and Lung Transplantation, Apr. 2011, 30(4):s55, 2 pages (Abstract Only).

Dieterlen et al., "Assay validation of phosphorylated S6 ribosomal protein for a pharmacodynamic monitoring of mTOR-inhibitors in peripheral human blood," Cytometry Part B: Clinical Cytometry, May 2012, 82(3)::151-157.

(Continued)

*Primary Examiner* — Michail A Belyavskyi

(74) *Attorney, Agent, or Firm* — Fish & Richardson P.C.

(57) ABSTRACT

This disclosure provides a potency assay for evaluating the potency of facilitating cells and/or alpha beta TCR+ T cells.

9 Claims, 5 Drawing Sheets

(56)         References Cited

OTHER PUBLICATIONS

Grimes et al., "Graft facilitating cells are derived from hematopoietic stem cells and functionally require CD3, but are distinct from T lymphocytes," Exp. Hematol., Oct. 2004, 32(10):946-954.

Matsui et al., "Inhibition of mitogen-induced proliferation of spleen lymphocytes is correlated with the induction of cell-mediated immunity in *Salmonella* infection in mice," FEMS Microbio Lett, Aug. 1993, 112(1):113-118.

Omary et al., "An 80 to 85 kilodalton human phosphoglycoprotein associated with cell activation," J. Immunol., Nov. 15, 1988, 141(10):3492-3497 (Abstract Only).

Yang et al., "T Cell Exit from Quiescence and Differentiation into Th2 Cells Depend on Raptor-mTORC1-Mediated Metabolic Reprogramming," Immunity, Dec. 13, 2013, 39(6):1043-1056.

Franklin et al, "Ligation of the T Cell Receptor Complex Results in Activation of the Ras/Raf-1/MEK/MAPK Cascade in Human T Lymphocytes," The Journal of Clinical Investigation, May 1, 1994, 93(5):2134-2140.

METHODS AND COMPOSITIONS FOR DETERMINING THE POTENCY OF A THERAPEUTIC CELLULAR COMPOSITION

TECHNICAL FIELD

This disclosure generally relates to methods and compositions for determining the potency of a therapeutic cellular composition.

BACKGROUND

Potency assays are intended to predict the therapeutic activity of a cellular composition by detecting or measuring one or more biological markers that are linked to one or more physiological properties. Because the therapeutic mechanisms of action can vary between therapeutic cellular compositions, however, it can be difficult to identify a biological function that is reproducibly linked to the relevant biological or biophysical properties. In addition, because the therapeutic mechanisms of action can rely on complex biological pathways, it can be especially challenging to identify which product attributes are most relevant to determining potency. Nonetheless, it is extremely important to develop potency assays that reflect the cellular compositions therapeutic properties and provide a reliable measure of production batch-to-batch consistency.

The present disclosure describes a novel potency assay for evaluating the therapeutic efficacy of graft facilitating cells (FCs) and/or alpha beta TCR+ T cells.

SUMMARY

Methods and compositions for evaluating the potency of facilitating cells and/or alpha beta TCR+ T cells are described herein.

In one aspect, a method of determining the potency of a sample that includes facilitating cells (FCs) and/or alpha beta TCR+ T cells is provided. Such a method typically includes contacting a sample including FCs and/or alpha beta TCR+ T cells with a mitogenic stimulus; and determining the number of FCs and/or alpha beta TCR+ T cells in the sample in which ribosomal S6 protein is phosphorylated (pS6). As described herein, the number of FCs and/or alpha beta TCR+ T cells in the sample in which pS6 is phosphorylated is indicative of the potency of the FCs and/or alpha beta TCR+ T cells, respectively, in the sample.

Representative mitogenic stimuli include, without limitation, phorbol 12-myristate 13-acetate (PMA) with ionomycin, phytohaemagglutinin (PHA), concanavalin A (conA), and pokeweed mitogen (PWM). In some embodiments, the sample is contacted with a mitogenic stimulus for a period of time from about 5 mins to about 60 mins (e.g., from about 20 mins to about 30 mins).

In some embodiments, the sample includes about 100,000 to about 2,000,000 FCs and/or alpha beta TCR+ T cells. In some embodiments, the number of FCs and/or alpha beta TCR+ T cells in the sample in which pS6 is phosphorylated is determined using a fluorescently-labeled antibody against pS6. In some embodiments, binding of the fluorescently-labeled antibody is detected using FACS.

In some embodiments, the method is performed prior to freezing the FCs and/or alpha beta TCR+ T cells. In some embodiments, the method is performed on FCs and/or alpha beta TCR+ T cells that have been frozen.

In some embodiments, at least 30% of the FCs in the sample are pS6+. In some embodiments, at least 30% of the alpha beta TCR+ T cells in the sample are pS6+.

In another aspect, a method of determining a therapeutic dose of FCs and/or alpha beta TCR+ T cells is provided. Such a method typically includes providing a cell sample including FCs and/or alpha beta TCR+ T cells; determining the potency of the cell sample. As described herein, the potency of the cell sample can be an indication of the therapeutic dose of FCs and/or alpha beta TCR+ T cells.

In another aspect, an article of manufacture that includes an antibody against the phosphorylated form of pS6 and at least one of the following: an antibody against CD3, an antibody against CD8, and an antibody against alpha beta TCR.

In some embodiments, the article of manufacture includes an antibody against the phosphorylated form of pS6, an antibody against CD3, and an antibody against alpha beta T cell receptor (TCR). In some embodiments, the article of manufacture includes an antibody against the phosphorylated form of pS6 and an antibody against CD8. In some embodiments, the article of manufacture includes an antibody against the phosphorylated form of pS6, an antibody against CD3, an antibody against CD8, and an antibody against alpha beta TCR.

An article of manufacture as described herein can further include a mitogenic stimulus. An article of manufacture as described herein can further include at least one fluorescent label. An article of manufacture as described herein can further include at least one fluorescent label for each antibody. In some embodiments, each of the at least one fluorescent label for each antibody are distinguishable from one another.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
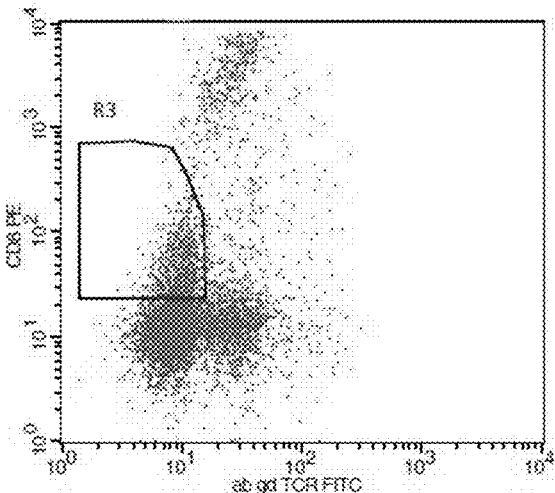
FIG. 1 shows the gating of FCs (CD8+/TCR−).

This disclosure provides for methods of determining the potency of FCs and/or alpha beta TCR+ T cells. FCs and alpha beta TCR+ T cells are two of the three primary components in a therapeutic cellular composition, which is described in U.S. Pat. Nos. 8,632,768 and 9,452,184. Given the current therapeutic and clinical use of this therapeutic cellular composition, a rapid and quantitative method to evaluate the potency of the therapeutic cellular composition and, more specifically, the FCs and alpha beta TCR+ T cells therein, after preparation and before administration to a patient, would be very useful.

During the preparation of a therapeutic composition of HSCs, FCs and alpha beta TCR+ T cells, or after such a therapeutic composition has been prepared, a sample of cells from the composition can be removed and contacted with a mitogenic stimulus. Typically, FCs and/or alpha beta TCR+ T cells (e.g., about FCs and/or alpha beta TCR+ T cells) are contacted with the mitogenic stimulus. As used herein, mitogenic stimuli, or simply mitogens, refer to compounds (e.g., proteins, small molecules, etc.) that trigger cells to undergo mitosis. Representative mitogenic stimuli include, without limitation, phorbol 12-myristate 13-acetate (PMA; also known as 12-O-tetradecanoylphorbol-13-acetate (TPA)) with ionomycin, phytohaemagglutinin (PHA), concanavalin A (conA), or pokeweed mitogen (PWM). In some instances, a commercially available cell stimulation cocktail can be used (e.g., Catalog No. 00-4970, ThermoFisher Scientific) under manufacturer's conditions. Alternatively, dilution or titration experiments can be performed to determine the amount and time of exposure of a particular mitogen that produces a maximal amount of stimulation and/or signal indicating potency in a therapeutic cellular composition as described herein.

Typically, about 100,000 to about 2,000,000 total cells (i.e., from a therapeutic cellular composition that includes HSCs, FCs, and alpha beta TCR+ T cells) are contacted with a mitogen, mixed well (e.g., vortexed), and maintained at a temperature of about 37° C. for about 5 minutes to about 60 minutes (i.e., one hour) (e.g., about 5 minutes to about 50 minutes; about 5 minutes to about 30 minutes; about 5 minutes to about 15 minutes; about 10 minutes to about 45 minutes; about 10 minutes to about 30 minutes; about 15 minutes to about 45 minutes; about 15 minutes to about 30 minutes; about 20 minutes to about 60 minutes; about 20 minutes to about 40 minutes; about 30 minutes to about 45 minutes; about 30 minutes to about 60 minutes; about 45 minutes to about 60 minutes). The length of time the FCs and/or alpha beta TCR+ T cells are exposed to a mitogenic stimuli depends, in part, on the particular mitogenic stimuli used; in some embodiments, the FCs and/or alpha beta TCR+ T cells are exposed to a mitogenic stimulus for about 15 minutes in a 5% $CO_2$ incubator set at 37° C.

After the cells have been stimulated with a mitogen for an appropriate length of time, the number of FCs and/or alpha beta TCR+ T cells in which the ribosomal S6 protein ("S6") is phosphorylated ("pS6") is determined. It would be appreciated that the most common and efficient method for determining the number of cells is to use one or more fluorescent antibodies and fluorescence activated cell sorting (FACS) analysis. In the present methods, differentially fluorescently-labeled antibodies can be used to stain stimulated cells with anti-CD3, anti-CD8, anti-alpha beta TCR and anti-phospho-S6 (i.e., anti-pS6). Total FCs are enumerated as CD8+ and alpha beta TCR+, while potent FCs are enumerated as CD8+, alpha beta TCR+ and phospho-S6+ (i.e., pS6+). Similarly, total alpha beta TCR+ T cells are enumerated as CD3+, while potent alpha beta TCR+ T cells are enumerated as CD3+ and pS6+. Antibodies that can be used in the methods described herein are commercially available. See, for example, BD Biosciences (e.g., Catalog Nos. 563423; 557757; 555916; 557760; 557746; 561951; 563625; 563826; 561674; 560433; 560434; or 560435); Abnova Corp. (e.g., Catalog Nos. MAB12370; MAB9820; MAB4591; MAB4596; ab99859; ab95648; MAB6560; or MAB6559); or eBiosciences (e.g., Catalog Nos. 12-0039; 50-0037; 25-0087; 9047-0087; 46-9986; 11-9986; 12-9007; or 48-9007).

A large number of fluorescent labels are known in the art that can be used with FACS. The large number of different labels, which can be categorized by the wavelength of light they emit (e.g., red, violet, yellow, green, blue), allows for simultaneous or concurrent detection of multiple antibodies and their corresponding binding targets. For example, the antibodies against CD3, CD8 and alpha beta TCR described herein can be differentially labeled so as to be able to distinguish FCs from alpha beta TCR+ T cells, and the antibody against the phosphorylated form of pS6 also can be differentially labeled from the other labeled antibodies so as to be able to distinguish phosphorylated S6 (i.e., pS6) from non-phosphorylated S6 FCs as well as phosphorylated S6 (i.e., pS6) from non-phosphorylated S6 alpha beta TCR+ T cells. Without limitation, representative fluorescent labels include, for example, Alexa fluor 488, Alexa fluor 532, Alexa fluor 647, Alexa fluor 700, Cyanine 5, Cyanine 5.5, Cyanine 7, Fluorescent isothiocyanate (FITC), Phycoerythrin (PE), eFluor 450, eFluor 506, eFluor 610, eFluor 660, and eFluor 780. Fluorescent labels can be obtained from, for example, EMD Millipore (Darmstadt, Germany); abcam (Cambridge, Cambridgeshire, UK); and Promega (Madison, WI).

For example, in a GMP (good manufacturing practices) production setting for clinical use, a small portion of the final therapeutic cellular composition can be contacted with the mitogenic stimulus for an appropriate period of time and then analyzed by FACS to determine the percent of FCs and alpha beta TCR+ cells that contain pS6. In some embodiments, about six million white blood cells are stimulated with a mitogen. Typically, of the 6 million white blood cells, about 250,000 cells are expected to be alpha beta TCR+ T cells and about 25,000 cells are expected to be FCs. Samples can be evaluated before cryopreservation and/or after cryopreservation and thawing. In the latter case, the sample to be evaluated for potency can be cryopreserved in a separate vial. Potency testing can be performed before patients are prepared for administration of the therapeutic cellular composition and can be used to determine whether the therapeutic cellular composition has sufficient cells to be administered. The methods described herein to determine the potency of FCs and/or alpha beta TCR+ T cells are quantitative and can be performed in about 2 to 4 hours, which make these methods very useful in the clinical setting.

As described herein, the number of FCs and/or alpha beta TCR+ T cells in the sample in which the S6 has been phosphorylated is an indicator of the potency of those cells in the sample. As used herein, "potency" refers to the number of cells in a sample that respond to the mitogenic stimulus by phosphorylating S6. Cells that respond in this way (i.e., by phosphorylating S6) are considered potent because they can respond to extracellular signals and initiate nuclear reprogramming in response to these signals. Determining the potency of cells (e.g., FCs and alpha beta TCR+ T cells) after preparation and/or any other type of manipulation (e.g., freezing, thawing, transporting/shipping) can be a critical component in the preparation of a therapeutic cellular composition and determining the biological quality of the therapeutic cellular composition. Importantly, the potency assay described herein also can be used to determine and quantify the stability of the therapeutic cellular composition during and/or after storage (e.g., cryopreservation).

With cell therapies, it is desirable to confirm or determine the potency of one or more of the cell types within a cellular composition. In the present case, it is desirable that at least about 30% of the FCs in a cellular composition are pS6+ (i.e., at least about 30% of the FCs in the sample are potent) or at least about 30% of the alpha beta TCR+ T cells in a cellular composition are pS6+(i.e., at least about 30% of the alpha beta TCR+ T cells in the sample are potent). In the present case, it is desirable that at least about 30% of the FCs in a cellular composition are pS6+(i.e., at least about 30% of the FCs in the sample are potent) and at least about 30% of the alpha beta TCR+ T cells in a cellular composition are pS6+(i.e., at least about 30% of the alpha beta TCR+ T cells in the sample are potent).

It would be understood that "at least 30%", as used herein with respect to the therapeutic cellular composition or any of the particular cell types therein, can refer to, for example, at least 35%, at least 40%, at least 45%, at least 50%, at least 55%, at least 60%, at least 65%, at least 70%, at least 75%, at least 80%, at least 85%, at least 90% or at least 95%. It also would be understood that reference to at least 30% can refer to, for example, about 30% to about 90%, about 30% to about 80%, about 30% to about 70%, about 40% to about 80%, about 40% to about 70%, about 40% to about 60%, about 50% to about 80%, about 50% to about 70%, about 60% to about 90%, about 60% to about 80%, about 70% to about 80%, about 75% to about 80%, or about 80% to about 90%.

In some instances, one or more documents (e.g., Certificates of Analysis) can accompany a therapeutic cellular composition. Documents that can be included with a therapeutic cellular composition can report, for example, one or more of the following: the total percentage of pS6+ or potent cells (relative to the total number of cells) in the therapeutic cellular composition; the percentage of pS6+ or potent FCs in the therapeutic cellular composition; the percentage of pS6+ or potent alpha beta TCR+ T cells in the therapeutic cellular composition; the number of pS6+ or potent FCs in the therapeutic cellular composition; and/or the number of pS6+ or potent alpha beta TCR+ T cells in the therapeutic cellular composition. Documents that can be included with a therapeutic cellular composition also can indicate a recommended dosage (e.g., a number of total cells, a number of pS6+ or potent cells, or a volume) and/or a dosing regimen.

The methods described herein, therefore, can be used to determine a suitable therapeutic dose of a cellular composition that includes FCs and/or alpha beta TCR+ T cells. For example, the potency of a sample of cells that includes FCs and/or alpha beta TCR+ T cells can be determined as described herein and, based on the potency of either or both the FC or the alpha beta TCR+ T cells, a therapeutic dose can be determined and subsequently administered to a patient. As used herein, a suitable therapeutic dose refers to a dose that allows engraftment in the absence of graft-vs-host-disease and in the absence of any toxicity (e.g., from the alpha beta TCR+ T cells).

This disclosure also provides for articles of manufacture. Articles of manufacture as described herein can include, for example, one or more of the antibodies described herein. For example, one or more antibodies that specifically bind to CD3, CD8, alpha beta TCR, and/or pS6 can be included in an article of manufacture as described herein.

Articles of manufacture as described herein also can include one or more fluorescent labels. It would be appreciated that a fluorescent label can be provided for each of the antibodies in the article of manufacture. It also would be appreciated that, when a fluorescent label is provided for each of the antibodies, each of those fluorescent labels can be different (e.g., distinguishable from one another). Further, one or more of the antibodies in an article of manufacture can be provided already labeled; alternatively, the fluorescent labels can be provided separately (e.g., in separate vials) from the antibodies for labeling by an end-user.

Articles of manufacture can include additional components such as, without limitation, one or more mitogens (e.g., phorbol 12-myristate 13-acetate (PMA) with ionomycin, phytohaemagglutinin (PHA), concanavalin A (conA), or pokeweed mitogen (PWM)), cell culture media, one or more buffers, reagents and/or co-factors. Articles of manufacture also can include one or more containers, e.g., vials, cuvettes, test tubes, culture plates, and the like, for performing the steps necessary for determining potency of FCs and/or alpha beta TCR+ T cells.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Principle of the Methods

The methods described herein can be used to determine the potency of the cryopreserved final product from the manufacturing process of the therapeutic cellular composition referred to herein as FCRx.

The mechanism of action of the facilitating cells (FC) and alpha beta TCR$^+$ cells is a complex process involving cellular migration, support of stem cell engraftment and the development of immune tolerance. The phosphorylation of a target ribosomal S6 protein (pS6) involved in protein synthesis and cell proliferation was developed as a surrogate assay to indicate that the FC and alpha beta TCR$^+$ cells were capable of responding to a mitogenic stimulus post-cryopreservation. The phosphorylation of S6 was quantitated in non-stimulated and stimulated cell samples stained with antibody panels for FC or alpha beta TCR$^+$ and the increase in pS6 with stimulation determined for both subsets of cells.

Immunophenotyping is the technique used to study proteins expressed by cells. It involves the labeling of cells with fluorescent antibodies directed against cell surface antigens or intracellular proteins. The labeled cells are analyzed on a flow cytometer, a laser-based instrument capable of analyzing thousands of cells per second in terms of size, cellular complexity, and fluorescence properties.

T cells exhibited CD3 on their cell surface. By using a mouse anti human CD3 antibody labeled with phycoerythrin (PE), a positive fluorescence signal was detected. The CD8 T-cell subset expressed CD8 on their cell surface. By using a mouse anti human CD8 antibody labeled with PE, a positive fluorescence signal was detected. T cells exhibited TCR (comprised of alpha beta and gamma delta subunits) on their cell surface. When labeled with fluorescein isothiocyanate (FITC) conjugated mouse anti human alpha beta TCR antibody, a positive fluorescence signal was detected. When labeled with FITC conjugated mouse anti human gamma delta TCR antibody, a positive fluorescence signal was detected. The alpha beta TCR$^+$ cells exhibited the phenotype alpha beta TCR$^+$ CD3$^+$. Facilitating cells (FC) exhibited the phenotype alpha beta TCR-gamma delta TCR-CD8$^+$. Stimulated cells expressed pS6 within the cell. By using an anti-pS6 antibody labeled with alexa fluor 647 (AF647), a positive fluorescence signal was detected.

Immunophenotyping for FC and alpha beta TCR$^+$ cells has been described. See, for example, U.S. Pat. Nos. 8,632, 768 and 9,452,184. Therefore, this disclosure focuses on the use of the phosphorylation of S6 as an indication of the potency of the FCs and alpha beta TCR+ T cells.

The qualification strategy utilized cryopreserved final product from a FCRx manufacturing process training run (Lot ICT-R&D052615). The samples were analyzed on a FACSCalibur flow cytometers (BD Biosciences) that had undergone acceptable installation, operation and performance qualifications.

The pS6 assay was qualified without use of a positive control (PC) or system suitability test (SST). Typically, the PC or SST would be a human cell stimulated with mitogen and the intracellular pS6 signal measured. However, the FCRx sample contained a heterogeneous mixture of cells, and we analyzed the phenotype of specific cell subpopulations of interest and assessed pS6 staining following mitogenic stimulation; therefore, the test sample acted as its own SST.

In addition, differences in response of a PC due to donor variability would also be a factor and there was no specific PC available from a commercial vendor. The use and implementation of an assay PC or SST will be further investigated during full validation but did not impact the qualification of the pS6 assay for use in assessing potency of the FCRx final product.

The following abbreviations were used:

TABLE 1

Abbreviations

| Abbreviations | Full Name |
|---|---|
| AF647 | alexa fluor 647 |
| CD | cluster of differentiation |
| CV | coefficient of variation |
| FC | facilitating cells |
| FITC | fluorescein isothiocyanate |
| IgG | immunoglobulin |
| IQOQPQ | Installation, operation and performance qualification |
| LOQ | limit of quantitation |
| na | not applicable |
| nd | no data |
| PC | positive control |
| PE | phycoerythrin |
| SD | standard deviation |
| SST | system suitability control |
| TCR | T cell receptor |
| WBC | white blood cells |
| % DIFF | % Difference = (% Cells TX − % Cells T0) × 100 % Cells T0 |

Example 2—Selectivity of pS6

The selectivity of the pS6 antibody was evaluated using FCRx final product to confirm that negative and positive fluorescence signals were obtained from non-stimulated and stimulated cells, respectively. Since non-stimulated cells demonstrated a low level of S6 phosphorylation (i.e., pS6), selectivity was also assessed by an increase in pS6 phosphorylation in stimulated cells. The selectivity of the pS6 antibody is shown by the increased frequency of FC cells (FIG. 1) that stain for pS6 in the stimulated sample (red curve) compared to the unstimulated sample (blue curve) (FIG. 2). The selectivity of the pS6 antibody is shown by the increased frequency of alpha beta TCR$^+$ cells (FIG. 3) that stain for pS6 in the stimulated sample (red curve) compared to the unstimulated sample (blue curve) (FIG. 4).

Figure 2:
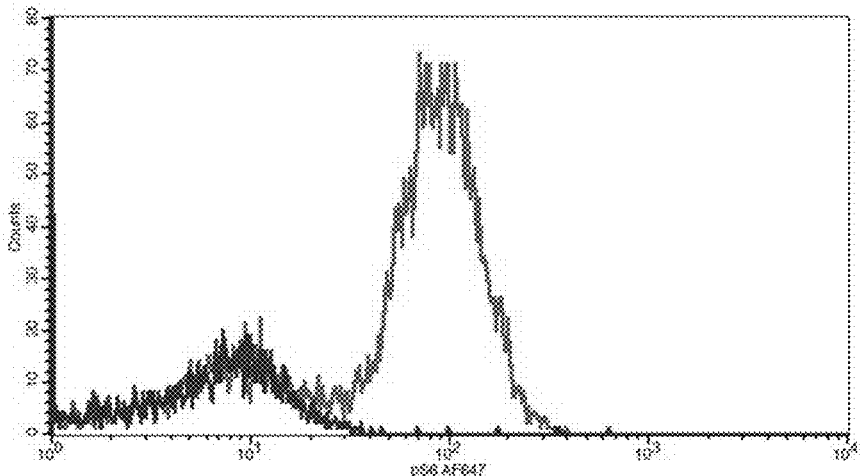
FIG. 2 is a graph showing the selectivity of pS6 for FCs.

With reference to FIG. 1, the FCs were clearly identified with the phenotype alpha beta TCR-gamma delta TCR$^-$ CD8$^+$ and were gated using the region R3. The pS6 staining of the FC was then assessed using a single parameter histogram.

With reference to FIG. 2, a representative overlay of the fluorescence distribution of unstimulated FC (blue curve) and stimulated FC (red curve) stained with pS6. The stimulated cells stained with pS6 antibody demonstrated clear separation (>1 log) of fluorescence intensity for the pS6$^+$ cells compared to the pS6$^-$ cells. The unstimulated sample had 24.81% pS6$^+$ cells with a mean fluorescence intensity (MFI) of 5.8. The stimulated sample had 78.94% pS6$^+$ cells with a MFI of 89.1, exhibiting a 15-fold increase in fluorescence compared to the pS6$^-$ cells.

Figure 3:
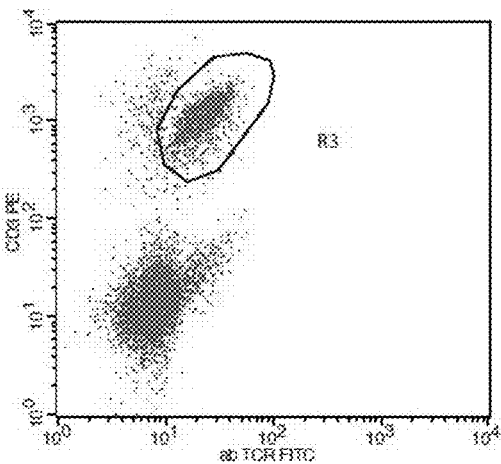
FIG. 3 shows the gating of alpha beta TCR+ cells.
Figure 4:
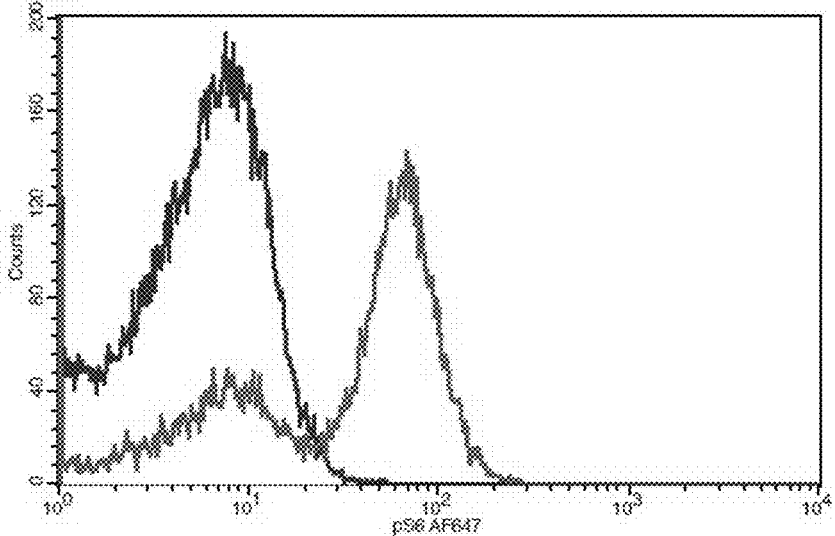
FIG. 4 is a graph showing the selectivity of pS6 for alpha beta TCR+ cells.

With reference to FIG. 3, the alpha beta TCR$^+$ cells were clearly identified with the phenotype alpha beta TCR$^+$/CD3$^+$ and were gated using the region R3. The pS6 staining of the alpha beta TCR$^+$ cells then was assessed using a single parameter histogram.

With reference to FIG. 4, a representative overlay of the fluorescence distribution of unstimulated alpha beta TCR$^+$ cells (blue curve) and stimulated alpha beta TCR$^+$ cells (red curve) stained with pS6. The stimulated cells stained with pS6 antibody demonstrated clear separation (>1 log) of fluorescence intensity for the pS6$^+$ cells compared to the pS6$^-$ cells. The unstimulated sample had 4.98% pS6$^+$ cells with a MFI of 5.27. The stimulated sample had 81.47% pS6$^+$ cells with a MFI of 62.99, exhibiting a 12-fold increase in fluorescence compared to the pS6$^-$ cells.

These data met the acceptance criteria for selectivity and indicate that the assay is specific for pS6.

Example 3—Accuracy of Methods

The accuracy of the pS6 assay was determined from the recovery of cells from the linearity assessment. Data are shown for pS6$^+$ FC (Table 2) using the results from linearity (Table 5).

TABLE 2

Accuracy pS6 - FC

| | Expected FC % pS6$^+$Cells | | | | | | | |
|---|---|---|---|---|---|---|---|---|
| | 62.10 | 31.05 | 15.53 | 7.76 | 3.88 | 1.94 | 0.97 | 0.49 |
| Recovery (background subtracted) | 100.0 | 99.9 | 101.9 | 106.4 | 104.3 | 94.8 | 113.7 | 116.1 |

The recovery of the pS6$^+$ FC cells ranged from 94.8% to 116.1% for the pS6$^+$ FC population of cells ranging from 62.1% to 0.49% of the FC subset. This indicates that the pS6 assay has an accuracy of within 16.1% of the nominal value. This met the target of value of ±30% of the calculation % pS6+ cells.

Example 4—Intra-Assay Precision

The intra-assay precision of the method was assessed from the four replicates from Analyst 1, Day 1, and Instrument 1. The data for the pS6$^+$ FC and alpha beta TCR$^+$ cells are shown in Table 3.

TABLE 3

| Intra-assay precision for % pS6+ FC and alpha beta TCR+ cells | | | | |
|---|---|---|---|---|
| | Assay: Intra-assay Precision | | | |
| | % pS6+ FC (unstimulated) | % pS6+ FC (stimulated) | % pS6+ alpha beta TCR+ T cells (unstimulated) | % pS6+ alpha beta TCR+ T cells (unstimulated) |
| Replicate 1 | 24.80 | 79.29 | 4.99 | 80.83 |
| Replicate 2 | 26.42 | 79.46 | 4.51 | 83.10 |
| Replicate 3 | 24.19 | 78.89 | 4.13 | 80.79 |
| Replicate 4 | 23.83 | 78.11 | 6.27 | 81.14 |
| Mean | 24.81 | 78.94 | 4.98 | 81.47 |
| SD | 1.146 | 0.601 | 0.932 | 1.101 |
| % CV | 4.6 | 0.8 | 18.7 | 1.4 |
| Acceptance Criteria | ≤30% | ≤30% | ≤30% | ≤30% |
| Outcome | Pass | Pass | Pass | Pass |

The % CV for the pS6+ cells in the unstimulated and stimulated samples from the four replicates of FCRx final product stained with the panels for the FC and alpha beta TCR+ cells were ≤30% and met the acceptance criteria.

Example 5—Intermediate Precision

The intermediate precision of the method was assessed from the data generated by two analysts over two days on two separate flow cytometers. The data for the pS6+ FC and alpha beta TCR+ cells are shown in Table 4.

TABLE 4

| Intermediate Precision for pS6+ FC and alpha beta TCR+ Cells | | | | | | | |
|---|---|---|---|---|---|---|---|
| Assay: Precision | Analyst | Instrument | Day | % pS6+ FC (unstimulated) | % pS6+ FC (stimulated) | % pS6+ + αβTCR cells (unstimulated) | % pS6+ + αβTCR cells (stimulated) |
| Replicate 1 | 1 | 1 | 1 | 24.80 | 79.29 | 4.99 | 80.83 |
| Replicate 2 | 1 | 1 | 1 | 26.42 | 79.46 | 4.51 | 83.10 |
| Replicate 3 | 1 | 1 | 1 | 24.19 | 78.89 | 4.13 | 80.79 |
| Replicate 4 | 1 | 1 | 1 | 23.83 | 78.11 | 6.27 | 81.14 |
| Replicate 5 | 2 | 1 | 1 | 0.56 | 44.32 | 1.53 | 60.09 |
| Replicate 6 | 2 | 1 | 1 | 0.41 | 47.81 | 1.71 | 51.05 |
| Replicate 7 | 1 | 2 | 2 | 27.58 | 65.45 | 4.93 | 76.57 |
| Replicate 8 | 1 | 2 | 2 | 26.46 | 71.43 | 4.73 | 77.46 |
| Replicate 9 | 2 | 2 | 2 | 29.30 | 80.05 | 4.56 | 85.57 |
| Replicate 10 | 2 | 2 | 2 | 30.33 | 78.25 | 3.50 | 85.58 |
| Replicate 11 | 2 | 2 | 2 | nd* | 80.78 | nd | 85.55 |
| Replicate 12 | 2 | 2 | 2 | nd | 79.49 | nd | 86.19 |
| Mean | | | | 21.39 | 71.94 | 4.09 | 77.83 |
| SD | | | | 11.212 | 12.881 | 1.477 | 11.035 |
| % CV | | | | 52.4 | 17.9 | 36.2 | 14.2 |
| Outcome | | | | na | na | na | na |

*nd = no data (see Deviation 2)

The % CV from the ten or twelve replicates of FCRx final product cells, analyzed over two days by two analysts using two cytometers, was 52.4% for the pS6+ FC (unstimulated), 17.9% for the pS6+ FC (stimulated), 36.2% for the pS6+ alpha beta TCR+ cells (unstimulated) and 14.2% for the pS6+ alpha beta TCR+ cells (stimulated). The results for analyst 2 day 1 demonstrated a lower % pS6+ for both the FC and alpha beta TCR+ unstimulated cells compared to those from analyst 1 day 1 and from both analysts on day 2. There was no acceptance criterion for intermediate precision, but data were reported as found.

Example 6—Linearity of pS6

Figure 5:
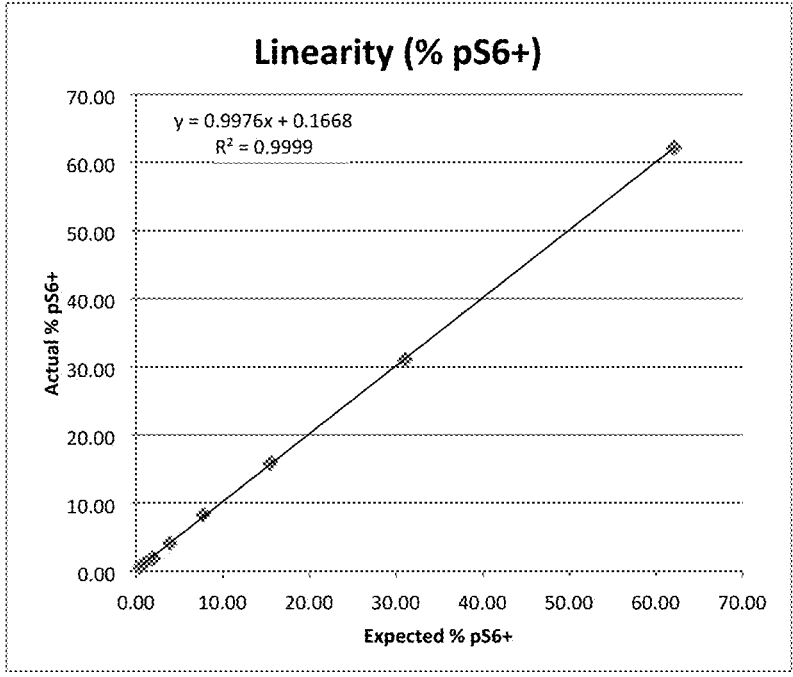
FIG. 5 shows the linear fit of pS6+ for FCs.

The linearity of the pS6 assay was determined by serial dilution of stimulated cells stained for the FC and pS6 with stimulated cells stained only for FC. The mean values of expected % phosphorylation were plotted as the independent variable versus phosphorylation as the dependent variable and a linear regression analysis using the equation $y=ax+b$ was applied (Table 5, FIG. 5, Table 6).

TABLE 5

| Summary of FC pS6+ Linearity Data | | | | | | | | |
|---|---|---|---|---|---|---|---|---|
| | Expected FC % pS6$^+$ Cells | | | | | | | |
| | 62.10 | 31.05 | 15.53 | 7.76 | 3.88 | 1.94 | 0.97 | 0.49 |
| Replicate 1 | 64.07 | 34.58 | 18.12 | 10.69 | 5.87 | 3.79 | 3.11 | 3.06 |
| Replicate 2 | 61.28 | 33.59 | 18.31 | 10.75 | 7.36 | 4.20 | 3.78 | 2.60 |
| Replicate 3 | 60.96 | 31.86 | 18.01 | 10.31 | 5.89 | 4.51 | 3.40 | 3.01 |
| Mean | 62.10 | 33.34 | 18.15 | 10.58 | 6.37 | 4.17 | 3.43 | 2.89 |
| SD | 1.711 | 1.377 | 0.152 | 0.239 | 0.855 | 0.361 | 0.336 | 0.252 |
| % CV | 2.8 | 4.1 | 0.8 | 2.3 | 13.4 | 8.7 | 9.8 | 8.7 |
| % Recovery | 100 | 107.4 | 116.9 | 136.3 | 164.2 | 214.7 | 353.5 | 595.7 |
| Mean (background subtracted) | 62.10 | 31.02 | 15.82 | 8.26 | 4.05 | 1.84 | 1.10 | 0.56 |
| Recovery (background subtracted) | 100.0 | 99.9 | 101.9 | 106.4 | 104.3 | 94.8 | 113.7 | 116.1 |

| pS6$^-$ Sample (background) | % cells in pS6$^+$ marker region |
|---|---|
| Replicate 1 | 2.19 |
| Replicate 2 | 2.18 |
| Replicate 3 | 2.61 |
| Mean | 2.33 |

In order to determine the linearity of the assay for detection of pS6$^+$ cells, the stimulated sample that was unstained for pS6 (pS6$^-$) was used to dilute out the pS6$^+$ cells. Due to autofluorescence of the cells, approximately 2.33% of the pS6$^-$ cells were captured in the marker region used to quantitate the % of pS6$^+$ cells. Therefore, this was subtracted from the overall mean % pS6$^+$ result and this mean value (background subtracted) was used to evaluate the linearity of the assay.

TABLE 6

| Linearity Fit Data for FC pS6+ Cells | | | |
|---|---|---|---|
| Parameter | Acceptance criteria | Result | Pass/Fail |
| Slope (a) | For information only | 0.9976 | Not applicable |
| Intercept (b) | For information only | 0.1668 | Not applicable |
| Correlation coefficient | ≥0.90 | 0.9999 | Pass |

Example 7—Robustness or Sample Stability

The stability of the pS6 staining was assessed by a hold time study using a cryopreserved FCRx final product sample. The sample was thawed, stained with the FC panel and pS6 and then divided into three separate aliquots. One aliquot was re-suspended in BD stain buffer and analyzed on the flow cytometer (Time 0 minutes, T0). Additional aliquots were fixed in 4% paraformaldehyde on ice and tested at 15 minutes (T15 min) after fixation and 20 hours (T20h) after storage at 2° C. to 8° C. Data for the T15 min was compared to the T0 time point, and data for the T20h time point was compared to the T15 min time point for changes in the % pS6$^+$ FC and calculated as % Difference (% DIFF) (Table 7). In addition, samples stained with the FC panel, the alpha beta TCR$^+$ cell panel and pS6 that were analyzed for intra-assay precision on day 1 were stored refrigerated overnight in the BD stain buffer and re-analyzed the next day (T21h). Due to the low volume of sample remaining after the primary analysis, these samples were pooled and reanalyzed as a single sample. Data for the T21h time point was compared to the mean T0 time point for changes in the % pS6+FC, % pS6+ alpha beta TCR$^+$ and calculated as % DIFF (Table 8).

$$\% \; DIFF = \frac{(\% \; cells \; TX - \% \; Cells \; T0)}{\% \; Cells \; T0} \times 100$$

The exact times for sample storage were based upon the start times for the analysis of the samples on the FACSCalibur which were recorded within the electronic listmode files.

TABLE 7

| Stability Data for pS6$^+$ FC (Fixed Samples) | | |
|---|---|---|
| | Assay: Stability pS6 | |
| Time Point | pS6$^+$ FC (% of FC) Unstimulated | pS6$^+$ FC (% of FC) Stimulated |
| T0 (BD stain buffer) | 18.04 | 43.09 |
| T15 min (fixative) | 12.39 | 33.45 |
| T20 h (fixative) | 13.29 | 34.14 |
| % DIFF T15 min vs T0 | −31.3 | −22.4 |
| % DIFF T24 h vs T15 min | 7.3 | 2.1 |

TABLE 8

| Stability Data for pS6$^+$ FC (BD Stain Buffer Samples) | | |
|---|---|---|
| | Assay: Stability pS6 | |
| Time Point | pS6$^+$ FC (% of FC) Unstimulated | pS6$^+$ FC (% of FC) Stimulated |
| T0 | 24.81 | 78.94 |
| T21 h | 12.12 | 77.91 |
| % DIFF T21 h vs T0 | −51.1 | −1.3 |

TABLE 9

Stability data for pS6⁺ αβTCR⁺ (BD stain buffer samples)

| Time Point | Assay: Stability pS6 | |
| | pS6⁺ αβTCR⁺ (% of αβTCR⁺) Unstimulated | pS6⁺ αβTCR⁺ (% of αβTCR⁺) Stimulated |
| --- | --- | --- |
| T0 | 4.98 | 81.47 |
| T21 h | 4.67 | 76.64 |
| % DIFF T21 h vs T0 | −6.1 | −5.9 |

Samples that were stored in 2% paraformaldehyde demonstrated a decrease in pS6⁺ FC in both unstimulated and stimulated samples. However, the fixed samples stored refrigerated for 20 h had comparable levels of pS6⁺ cells compared to the samples 15-minutes post-fixation.

Samples that were stored overnight in the BD stain buffer had comparable levels of pS6⁺ FC and pS6⁺ alpha beta TCR⁺ cells compared to the same samples analyzed the previous day.

Example 8—Range and Limit of Quantitation

The pS6 phosflow potency assay demonstrated linearity with acceptable precision down to 0.56% pS6⁺ cells using the FC staining panel. Since the FC are typically a lower frequency subset of cells than the alpha beta TCR⁺ cells, linearity was determined for pS6 using the FC panel and applied to both the FC and the alpha beta TCR⁺ cells. The upper range of pS6⁺ cells tested was 62.10%, which was the level of pS6 phosphorylation observed in the undiluted pS6⁺ stimulated FC sample for that assay with precision of 2.8% CV for the three replicate samples tested. It may, therefore, be assumed that final product with pS6⁺ cell frequencies higher than those tested in this qualification would also demonstrate acceptable linearity since higher frequencies of events show statistically lower variability. Therefore, the range of the pS6 phosflow assay is 0.56% to 100% pS6⁺ cells with an LOQ of 0.56%.

Example 9—Threshold for Potency

This assay qualification utilized one representative lot of FCRx final product with multiple vials of test material thawed and analyzed over three days of testing. The pS6 potency assay requires specific criteria to be applied to the pS6 phosphorylation in the FC and alpha beta TCR⁺ cells in order to determine whether the cells are potent. This may be determined by either the total increase in the pS6⁺ cells in the stimulated sample compared to the unstimulated sample (% pS6⁺ stimulated minus % pS6⁺ unstimulated) or by a factorial increase in the pS6⁺ cells in the stimulated sample compared to the unstimulated sample by calculation of a stimulation factor (% pS6⁺ stimulated/% pS6⁺ unstimulated). The results from the precision testing were assessed for both of these threshold determinations and are summarized in Table 10 and Table 11. The results for analyst 2 day 1 were omitted as they were possible outliers and for analyst day 2 were omitted where replicate unstimulated samples were not analyzed as detailed in Deviation 2.

TABLE 10

Potency threshold - FC

| | Assay: Precision | | | |
| | % pS6⁺ FC (unstimulated) | % pS6⁺ FC (stimulated) | Total pS6⁺ increase % pS6⁺ Stimulated − % pS6⁺ Unstimulated | Factorial pS6⁺ increase % pS6⁺ Stimulated\ % pS6⁺ Unstimulated |
| --- | --- | --- | --- | --- |
| Replicate 1 | 24.80 | 79.29 | 54.49 | 3.2 |
| Replicate 2 | 26.42 | 79.46 | 53.04 | 3.0 |
| Replicate 3 | 24.19 | 78.89 | 54.70 | 3.3 |
| Replicate 4 | 23.83 | 78.11 | 54.28 | 3.3 |
| Replicate 7 | 27.58 | 65.45 | 37.87 | 2.4 |
| Replicate 8 | 26.46 | 71.43 | 44.97 | 2.7 |
| Replicate 9 | 29.30 | 80.05 | 50.75 | 2.7 |
| Replicate 10 | 30.33 | 78.25 | 47.92 | 2.6 |
| Mean | | | 49.75 | 2.89 |
| SD | | | 5.936 | 0.342 |
| % CV | | | 11.9 | 11.8 |

The total pS6⁺ increase for the FC was 49.75% pS6⁺ cells and the stimulation factor was 2.89.
SD, standard deviation;
CV, coefficient of variation

TABLE 11

Potency Threshold - alpha beta TCR+ Cells

| | Assay: Precision | | | |
| | % pS6⁺ + αβTCR cells (unstimulated) | % pS6⁺ + αβTCR cells (stimulated) | Total pS6⁺ increase % pS6⁺ Stimulated − % pS6⁺ Unstimulated | Factorial pS6⁺ increase % pS6⁺ Stimulated\ % pS6⁺ Unstimulated |
| --- | --- | --- | --- | --- |
| Replicate 1 | 4.99 | 80.83 | 75.84 | 16.2 |
| Replicate 2 | 4.51 | 83.10 | 78.59 | 18.4 |
| Replicate 3 | 4.13 | 80.79 | 76.66 | 19.6 |
| Replicate 4 | 6.27 | 81.14 | 74.87 | 12.9 |

TABLE 11-continued

Potency Threshold - alpha beta TCR+ Cells

Assay: Precision

|  | % pS6+ +<br>αβTCR cells<br>(unstimulated) | % pS6+ +<br>αβTCR cells<br>(stimulated) | Total pS6+ increase<br>% pS6+ Stimulated −<br>% pS6+ Unstimulated | Factorial pS6+ increase<br>% pS6+ Stimulated\<br>% pS6+ Unstimulated |
|---|---|---|---|---|
| Replicate 7 | 4.93 | 76.57 | 71.64 | 15.5 |
| Replicate 8 | 4.73 | 77.46 | 72.73 | 16.4 |
| Replicate 9 | 4.56 | 85.57 | 81.01 | 18.8 |
| Replicate 10 | 3.5 | 85.58 | 82.08 | 24.5 |
| Mean |  |  | 76.68 | 17.78 |
| SD |  |  | 3.714 | 3.423 |
| CV |  |  | 4.8 | 19.2 |

The total pS6+ increase for the αβTCR+ cells was 76.68% pS6+ cells and the stimulation factor was 17.78.

Example 10—Deviations from the Validation Protocol

There were two deviations from the validation protocol.
Deviation 1

The $CO_2$ incubator used in the qualification had not undergone the IQOQPQ. The incubator temperature and $CO_2$ were monitored during the assay qualification activities using the readouts on the incubator. In addition, the temperature and $CO_2$ were monitored using a calibrated thermometer and temperature probe, and Fyrite kit prior to and after the qualification testing activities. All temperature and $CO_2$ readings were within required operating specifications for the incubator and the cells were stimulated and expressed pS6 indicating that the operating conditions of the incubator were appropriate. Therefore, this deviation had no impact on the quality or integrity of the data.
Deviation 2

The analyst 2 had insufficient cells to prepare the two sets of replicate samples for intermediate precision on day 2. The duplicate set of unstimulated cells for the FC and alpha beta TCR+ cells were eliminated. The duplicate stimulated cells were prepared with 300 µL of sample per tube and the volume of antibody used for cell surface staining was adjusted accordingly. The overall assessment of the intermediate precision was made using n=10 samples for the unstimulated cells and n=12 samples for the stimulated cells. Therefore, this deviation had no impact on the quality or integrity of the data.

Example 11—Discussion and Summary

The results from the qualification tests demonstrated that the pS6 antibody used in the phosflow potency assay was selective. The pS6AF647 antibody demonstrated a positive peak with a fluorescence separation of more than 1 log decade when compared to the pS6− cell population in the same sample. The pS6 phosphorylation was increased in all stimulated samples compared to the unstimulated control. The ability to detect the FC and alpha beta TCR+ cells was not compromised by the intracellular phosflow staining procedure so the phosphorylation of pS6 was quantitated in these two cell subpopulations. These data indicate that the fluorochrome-conjugated antibody clones that recognize the specific cell surface antigens and the pS6 may be used in combination in the pS6 phosflow potency assay.

The pS6 phosflow assay demonstrated an intra-assay precision of 4.8% CV and 0.8% CV for the unstimulated and stimulated FC panel samples, respectively, and 18.7% CV and 1.4% CV for the unstimulated and stimulated alpha beta TCR+ cell panel samples, respectively. These data were within the acceptance criteria of ≤30% CV. The intermediate precision, measured by two analysts using two cytometers on two days was 52.4% CV and 17.9% CV for the unstimulated and stimulated FC, respectively, and 36.2% CV and 14.2% CV for the unstimulated and stimulated alpha beta TCR+ cells, respectively. There were no acceptance criteria for intermediate precision and are reported as found. However, we did observe lower % pS6+ results for analyst 2 on day 1 of precision testing compared with the results from analyst 1 on days 1 and 2 and analyst 2 on day 2. This was determined to be due to the cells not being re-suspended sufficiently during the pS6 staining step and indicates that there are critical steps within the assay procedure that may contribute to assay variability. Although the intermediate precision was high for the unstimulated samples (36.2% to 52.4% CV), the stimulated samples demonstrated intermediate precision from 14.2% CV to 17.9% CV. This is representative of one lot of FCRx final product and the variability of the assay will need to be further assessed using additional final product lots to determine the overall variability between donors and manufacturing processes as well as the variability that may be introduced during the thawing procedure of the cryopreserved test samples.

The assay demonstrated linearity based upon a correlation coefficient≥0.90, CV of the replicates≤30% and recovery within ±30% of the expected value down to 0.56% pS6+ cells. The upper limit of linearity was dependent upon the relative frequency of the individual population of pS6+ cells present in the qualification test material which was 62.10% pS6+ cells for the linearity test. It may, therefore, be assumed that final product with pS6+ cell frequencies higher than those tested in this qualification would also demonstrate acceptable linearity since higher frequencies of events show statistically lower variability. Therefore, linearity and range may be assumed to be from 0.56% pS6+ cells up to 100% pS6+ cells. The linearity was assessed using only the FC panel, as this subpopulation typically has a lower frequency of events than the alpha beta TCR+ cells and, therefore, represents a more stringent assessment of the linearity of the assay. These data will therefore be used to apply criteria for the linearity of pS6 phosphorylation in both the FC and alpha beta TCR+ cells.

Since there were no commercially available control cells for the accuracy assessment of the pS6+ cells, accuracy was assessed from the expected recovery of the cells determined during linearity testing. The neat sample of pS6+ cells had 62.10% pS6+ cells and was, therefore, assumed to be the nominal value. The actual recovery of the pS6+ cells from the subsequent serial dilutions was compared to the expected result and the accuracy of the measurement was determined. Based upon the linearity results, accuracy within ±30% of nominal was demonstrated down to 0.56% pS6+ FC, which was the assigned LOQ of the assay. Therefore, these data indicate that the method is accurate for the detection of pS6+ FC and alpha beta TCR+ cells.

Sample stability was tested for samples that were stored refrigerated overnight in the BD stain buffer and also for samples that were stored in a cell fixative (2% paraformaldehyde). The cells are all fixed after the surface staining and stimulation step in the pS6 staining procedure, but this robustness assessment evaluated the storage of the final sample in BD stain buffer as per the method or storage in 2% paraformaldehyde fixative. For the FC samples that were stored in fixative, the 15-minute fixation resulted in a loss of pS6+ cells by up to 31.3% compared to the sample stored in BD stain buffer. However, subsequent storage of the sample for 21 h in the refrigerator showed no additional loss of pS6+ cells. For the samples stored refrigerated in BD stain buffer, there was a loss of 51.1% and 1.3% of pS6+ cells in the unstimulated and stimulated FC samples, respectively. The alpha beta TCR+ cell samples stored in BD stain buffer indicated a loss of up to 6.15% pS6+ cells after storage for 21 h in BD stain buffer. These data indicate that pS6 phosflow assay samples should be run on the flow cytometer on the day of preparation.

The threshold for potency was assessed by comparing the % pS6+ cells in the stimulated sample to that in the unstimulated sample for both the FC and alpha beta TCR+ cells. The FC demonstrated a total increase in % pS6+ cells of 49.75% following stimulation and a factorial increase of 2.89. The alpha beta TCR+ cells demonstrated a total increase in % pS6+ cells of 76.68% following stimulation and a factorial increase of 17.78. For the lot of FCRx final product tested, the alpha beta TCR+ cells exhibited a greater pS6+ phosophorylation following stimulation compared to the FC indicating that each cell type will require specific criteria for the threshold for potency. The assay qualification utilized only one lot of FCRx final product and some variability was observed between different vials of the same lot when thawed and analyzed as well as variability between analysts. Therefore, the following thresholds for potency (Table 12) are proposed based upon data from this qualification and will be further assessed and refined utilizing data to be collected from analysis of additional FCRx final product lots from research studies, phase II clinical manufacturing and assay validation.

TABLE 12

| Potency Thresholds | |
| --- | --- |
| Cell population | Threshold Total pS6+ Increase [Stimulated − unstimulated] |
| FC | 10% |
| Alpha beta TCR+ cells | 10% |

This method to assess the potency of the FC and alpha beta TCR+ cells in the FCRx final product is considered qualified. The assay is selective, accurate, and precise, with a limit of quantitation of 0.56% pS6+ cells and a range of 0.56% to 100% pS6+ cells. Samples should be analyzed on the day of preparation.

Example 12—Clinical Application

Cryovials of final product were thawed and the potency assays were used to determine functionality or potency of the T cells and FCs in the final product. These results were correlated with cell viability assays performed using 7AAD and trypan blue.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of preparing a therapeutic cellular composition, the method comprising:

providing a therapeutic cellular composition comprising FCs and/or alpha beta TCR+ T cells;

contacting a sample of the therapeutic cellular composition with a mitogenic stimulus for a period of time from about 5 minutes to about 60 minutes, wherein the sample comprises about 100,000 to about 2,000,000 FCs and/or alpha beta TCR+ T cells;

determining a number of FCs and/or alpha beta TCR+ T cells in the sample in which ribosomal S6 protein is phosphorylated (pS6+); and preparing the therapeutic cellular composition for delivery to a patient when at least 30% of the FCs and/or the alpha beta TCR+ T cells in the sample are pS6+.

2. The method of claim 1, wherein the mitogenic stimulus is selected from the group consisting of phorbol 12-myristate 13-acetate (PMA) with ionomycin, phytohaemagglutinin (PHA), concanavalin A (conA), and pokeweed mitogen (PWM).

3. The method of claim 1, wherein the sample is contacted with the mitogenic stimulus for a period of time from about 20 mins to about 30 mins.

4. The method of claim 1, where the number of FCs and/or alpha beta TCR+ T cells in the sample in which pS6 is phosphorylated is determined using a fluorescently-labeled antibody against pS6.

5. The method of claim 4, wherein binding of the fluorescently-labeled antibody is detected using FACS.

6. The method of claim 1, wherein at least 30% of the FCs in the sample are pS6+.

7. The method of claim 1, wherein at least 30% of the alpha beta TCR+ T cells in the sample are pS6+.

8. The method of claim 1, wherein the method is performed prior to freezing the FCs and/or alpha beta TCR+ T cells.

9. The method of claim 1, wherein the method is performed on FCs and/or alpha beta TCR+ T cells that have been frozen.

* * * * *